(12) United States Patent
Reginster et al.

(10) Patent No.: US 7,393,649 B2
(45) Date of Patent: Jul. 1, 2008

(54) DETECTION OF SPECIFIC NITRATED MARKERS

(75) Inventors: Jean-Yves Reginster, Angleur (BE); Michelle Deberg, Embourg (BE); Yves Henrotin, Beaufays (BE); Stephan Christgau, Gentofte (DK)

(73) Assignee: Universite de Liege, Liege (BG)

( * ) Notice: Subject to any disclaimer, the term of this patent is extended or adjusted under 35 U.S.C. 154(b) by 267 days.

(21) Appl. No.: 10/507,479

(22) PCT Filed: Mar. 12, 2003

(86) PCT No.: PCT/EP03/02559

§ 371 (c)(1),
(2), (4) Date: Sep. 13, 2004

(87) PCT Pub. No.: WO03/076946

PCT Pub. Date: Sep. 18, 2003

(65) Prior Publication Data
US 2005/0176081 A1    Aug. 11, 2005

(30) Foreign Application Priority Data
Mar. 13, 2002  (DK)  .................. PA 2002 00381

(51) Int. Cl.
 G01N 33/53   (2006.01)
 G01N 33/68   (2006.01)
 A61K 38/39   (2006.01)
(52) U.S. Cl. .................. 435/7.1; 436/110; 530/356; 530/840
(58) Field of Classification Search ................ 435/7.1; 436/110; 530/356, 840
See application file for complete search history.

(56) References Cited

U.S. PATENT DOCUMENTS

| 5,919,634 A | 7/1999 | Eyre | 435/7.1 |
|---|---|---|---|
| 6,132,976 A | 10/2000 | Poole et al. | 435/7.1 |
| 2002/0022244 A1 | 2/2002 | Kim et al. | 435/25 |

FOREIGN PATENT DOCUMENTS

| WO | WO96/04311 | 2/1996 |
|---|---|---|
| WO | WO98/29452 | 7/1998 |
| WO | WO01/38872 | 5/2001 |
| WO | WO 01/84160 A2 * | 11/2001 |

OTHER PUBLICATIONS

Harlow, E. and Lane, D., Antibodies: A Laboratory Manual (1988) Cold Spring Harbor Laboratory Press, Cold Spring Harbor, NY, pp. 23-25 and 76.*
Manicourt et al. Chapter 25, "Products of Cartilage Metabolism", In: Dynamics of Bone and Cartilage Metabolism (2006), Eds. Markus J. Seibel et al., Academic Press, pp. 421-449.*
Deberg et al. "New serum biochemical markers (Coll 2-1, and Coll 2-1 NO2) for studying oxidative-related type II collagen network degradation in patients with osteoarthritis and rheumatoid arthritis" OsteoArthritis and Cartilage (2005) 13, 258-265.*
Ter Steege et al. "Nitrotyrosine in Plasma of Celiac Disease Patients as Detected by a New Sandwich ELISA" Free Radical Biology & Medicine (1998) vol. 25, pp. 953-963.*
de Vries et al. "Specific localization of IgG isolated from inflamed synovial tissue" Agents and Actions vol. 19 (1986) pp. 5-6.*
Khan et a. "3-Nitrotyrosine in the proteins of human plasma determined by an ELISA method" Biochem J. (1998) 330, 795-801.*
Lin et al, Chemico-Biological Interaction 127, 2000, pp. 219-236, Nitration and hydoxylation of aromatic amino acid . . . .
Lotz, OSTEOARTHRITIS, vol. 25, No. 2, May 1999, pp. 269-282, The Role of Nitric Oxide in Articular Cartilage Damage.
Moller, Scand J. Clin Lab Invest, 58, 1998, pp. 269-278, Connective tissue markers of rheumatoid arthritis.
Paik et al, Connective Tissue Res, vol. 42(2) , pp. 111-122, 2001, The Nitrite/Collagen Reaction: Non-Enzymatic Nitration . . . .
Soinila et al, Jour of Histochem and Cytochem, vol. 40, No. 2, pp. 231-239, 1992, Immunohistochemistry of Enkephalins: . . . .
Stadtman et al, Anals NY Acad of Sciences, pp. 191-208, 2000, Protein Oxidation.
Wollheim, APMIS 104, 1996, pp. 81-93, Predictors of joint damge in rheumatoid arthritis.

* cited by examiner

*Primary Examiner*—Long Le
*Assistant Examiner*—Christine Foster
(74) *Attorney, Agent, or Firm*—Jacobson Holman PLLC

(57) ABSTRACT

Methods are described for improving the diagnostic possibilities of diseases where oxidative NO-modifications occur, for example inflammatory conditions, cancer, Parkinson's or Alzheimer's disease, and to provide means of monitoring the effects of therapeutical measures taken towards such diseases. The invention enables the detection of disease specific catabolic markers related to oxidative NO-modifications, utilizing an immunoassay comprising antibodies directed against nitrated and non-nitrated epitopes characteristic of a specific protein.

1 Claim, 5 Drawing Sheets

US 7,393,649 B2

DETECTION OF SPECIFIC NITRATED MARKERS

This is a nationalization of PCT/EP03/02559 filed Mar. 12, 2003 and published in English.

BACKGROUND OF THE INVENTION

The present invention relates to a method for performing a qualitative or quantitative assay which may be used for detecting quantifying or monitoring oxidative damage especially in relation to an inflammatory condition. Detection of nitrated specific proteins or fragments thereof versus equivalent non-nitrated proteins or fragments thereof, may serve as an index for oxidative damage in for example inflammatory bowel disease, systemic lupus erythematosus, arthritis, cancer, Parkinson's or Alzheimer's disease.

Throughout a lifetime organisms are challenged with numerous events and conditions that generate reactive oxygen species (ROS). An increase in an organism's rate of ROS production or a decrease in their rate of scavenging will increase the oxidative modification of cellular molecules, including DNA and proteins. Oxidation may have deleterious effects on protein function and stability. Many enzymes have been shown to lose their biological activity as a consequence of oxidation. Other effects of oxidation are lowered temperature-stability and changes in protein susceptibility towards proteolysis; the latter might lead to an accumulation of oxidized proteins unable to undergo degradation. Protein oxidation may be implicated in the pathogenesis of several diseases such as neurodegenerative diseases, cancers, arteriosclerosis, cataractogenisis, dysplasia, dystrophia and inflammatory diseases as well as in normal ageing.

Some of the common ROS generating processes and systems known to modify proteins are irradiation, inflammation, metal catalysed reactions such as Fe(II) or Cu(I) reduction and various other oxidizing compounds or free radicals, including nitric oxide (NO), peroxyitrite, $H_2O_2$ or hydroxyl, hydroperoxyl superoxide and lipid peroxyl radicals. A number of ROS are formed by specific enzyme systems such as nitric oxide synthetase (NOS), cyclo-oxygenase and mono-amine oxidase B, whereof some are induced under inflammatory conditions.

Under normal conditions the oxidative potential in the micro-environment of an organism is under tight control by a number of balancing systems including antioxidants, free radical scavengers, reductases, peroxidases, catalase, glutathione-S-transferase, super-oxide dismutase and various metal-binding proteins. These systems can be viewed as protection mechanisms, more than repair systems. Actual repair mechanisms specific for oxidative damaged proteins are rare, whereas the oxidative damage to nucleic acids is subject to highly efficient repair systems (Stadtman and Levine 2000).

Nitric oxide (NO) is produced in many tissues and regulates diverse functions, such as smooth muscle relaxation, non-specific defence against microorganisms, neurotransmitter and a possible modulator of the cartilage matrix. Nitric oxide synthetase (NOS) is responsible for the production of NO. There are two classes of NOS, a constitutive (cNOS) and an inducible (iNOS) form. iNOS activity appears in response to various cytokines, and produces a much larger amount of NO than cNOS. iNOS activity is thought to account for the proinflammatory effects of NO, as seen in conditions such as inflammatory bowel diseases, spontaneous gut inflammation, cardiovascular inflammation and arthritic diseases (osteoarthritis (OA) or rheumatoid arthritis (RA)).

The large cytotoxicity of NO is partly due to its ability to react with superoxide anion ($O_2^-$) to generate peroxynitrite anion ($ONOO^-$) and its conjugate acid, peroxynitrous acid (ONOOH). At neutral pH $ONOO^-$ is partly protonated, generating ONOOH, which rapidly decomposes to nitrate. These strong oxidants might seriously compromise cellular regulation, as it is capable of nitrating aromatic compounds like free phenylalanine, tyrosine and tryptophan as well as peptide chains containing these amino acids. This result in nitrophenylalanine, nitro-tryptophan and nitrotyrosine, the later can also be generated through the combined hydroxylation and nitration of a phenylalanine residue (Lin et al 2000). The nitration is irreversible and inhibits the phosphorylation of tyrosine and tryptophan residues, thus interfering with signal transduction pathways.

In OA and RA, NO is produced in large amounts by chondrocytes, macrophages and inflamed synovium. A high level of nitrite/nitrate has been found in the synovial fluid, serum and urine of patients with OA and RA (Lotz 1999). However, elevated NO levels cannot be considered a specific marker for any given disease or condition, as several different processes and tissues can give rise to systemic elevated NO levels.

The major clinical manifestation of RA as well as OA is an abnormal and degraded cartilage. However, until now it has been difficult to directly assess the ongoing cartilage destruction in arthritis patients, because specific markers for this process have not been available in the clinical practice. At clinical diagnosis of OA and RA, damage to cartilage in joints is recorded by X-ray, which reveals a loss of joint space as cartilage is destroyed and lost. Furthermore the patients are scored according to the pain and mobility problems caused by the joint destruction, but even though a number of standardised rating systems have been introduced, it is difficult to quantify these parameters. Other markers used for assessment of RA patients, such as C-reactive protein and Rheumatoid factors are associated with the inflammatory process involved in the disease, but are probably not directly related to the level of cartilage destruction and they are not specific for RA.

Detection of metabolites, such as cartilage oligomeric matrix protein (COMP), hyaluronates, aggrecan and collagen type II or III fragments arising from destruction of joints affected by inflammatory disease have been reported (Moller 1998, Wollheim 1996, U.S. Pat. No. 5,919,634, U.S. Pat. No. 6,132,976 and PCT application WO 01/38872). The clinical usefulness of these markers, however, remains to be proven.

The detection of $NO_2$-modified amino acids is known from the PCT patent applications WO 96/04311 and WO 98/29452. These patent applications disclose the sequence independent detection of a nitrotyrosine or a nitro-tryptophan residue in a protein or in its free form using an antibody, which specifically recognizes the nitro-group. Such an antibody might be used to assess a pathological condition relating to an abnormal level of nitrotyrosine. However the antibody will not be able to assess the problem in relation to a specific tissue or protein as it recognizes nitrotyrosine independent of the surrounding amino acid sequence.

SUMMARY OF THE INVENTION

The present invention relates to methods for quantifying $NO_2$-modified amino acids within the specific context of a protein or fragments thereof. Determination of such nitrated specific proteins or fragments thereof enables an assessment of oxidative damage and metabolic state of the given protein. This provides diagnostic assays, which associate metabolic changes and oxidative damage in specific diseases.

According to the present invention there is provided a method for performing a qualitative or quantitative assay for protein oxidation, comprising detecting in a sample an amino acid sequence which is characteristic of a specific protein and which contains one or more aromatic amino acid residues in nitrated form. This includes a method for detecting oxidative damage in a mammal. The method may comprise monitoring oxidative damage by detecting one or more nitrated aromatic residues in combination with an amino acid sequence specific to a protein or peptide, preferably specific to a certain tissue, in a biological sample. Preferred aromatic amino acid residues are nitrotyrosine and/or nitrotryptophan.

The method of the present invention can be applied for monitoring a pathological process involving an oxidative damage correlating with non-inflammatory diseases like arteriosclerosis, cancer, Alzheimer's disease, Parkinson's disease or inflammatory diseases like asthma, cardiovascular inflammation, diabetes, inflammatory bowel disease, psoriasis, systemic lupus erythematosus, arthritis.

The method of the present invention will enable the monitoring of a catabolic process of a joint tissue by measuring a protein or peptide derived from the extra cellular matrix of cartilage, joint synovium or subchondral bone. Such a protein might be collagen types I, II, III, VI, IX or XI, aggrecan, biglycan, chondromodulin, cartilage link protein, cartilage oligomeric matrix protein, cartilage intermediate layer protein or a fragment thereof, wherein a nitrotyrosine and/or nitrotryptophan residue is located.

The detection performed in the method of the present invention may be carried out using an antibody, which specifically binds a nitrated epitope comprising at least one nitrated aromatic amino acid residue in conjunction with a specific amino acid sequence.

The detection performed in the method of the present invention can also be carried out utilizing two antibodies, one which is specific for the nitrated aromatic amino acid residue in a context independent manner and one which recognizes the specific amino acid sequence.

The detection methods of the present invention can be performed in a way that generate an index of oxidative damage/inflammation, by using a second antibody, which specifically binds a non-nitrated amino acid sequence equivalent to the nitrated sequence bound by the antibody which recognizes the nitrated epitope described above, thereby generating a ratio between a specific nitrated and non-nitrated protein or peptide.

Alternatively, the relative amounts of nitrated and non-nitrated protein or peptide may be differently expressed, for instance as a difference or as the ratio of the nitrated content to the total of nitrated and non-nitrated content.

The index of oxidative damage/inflammation generated by application of the present invention, to a sample from a mammal, can be used to provide means for diagnosis or assessment of the severity of a disease involving oxidative damage, especially joint tissue diseases. For these purposes a kit utilizing an antibody, which recognizes a nitrated epitope and a second antibody recognizing the similar non-nitrated epitope, together with suitable labels, is provided. A supplement to such a kit is a peptide, which contains a succession of amino acids equivalent to the binding epitope for one of the mentioned antibodies, for competition assays. The kits of the present invention can be applied to samples like mammalian body fluids, extracts from cells or tissues or supernatants from cells or tissues cultured in vitro.

The present invention especially relates to detection of nitrated collagen type II protein, wherein the nitrated amino acid is the tyrosine of one of the sequences His-Arg-Gly-Tyr-Pro-Gly-Leu-Asp-Gly (SEQ ID NO: 1) or Leu-Gln-Tyr-Met-Arg-Ala (SEQ ID NO: 2). Synthetic nitrated peptides including these sequences may be used to raise polyclonal and/or monoclonal antibodies, as well as cell lines producing such monoclonal antibodies.

The present invention is based upon a new approach for development of diagnostic and prognostic assays for monitoring pathological conditions in of mammalian tissues, combining metabolic tissue specific markers with the state of an oxidative/inflammatory condition. One of the key effects of oxidative damage is nitration of aromatic amino acid residues such as phenylalanine, tyrosine or tryptophan. The presence of one or more nitrated aromatic amino acid residues in or near a marker specific to a certain tissue or disease, provides information about the metabolic state of a tissue from which a marker originates as well as the oxidative condition of the same tissue.

As used herein, "immunological binding partner" includes polyclonal, monoclonal or humanized antibodies, including Fc fragments, Fab fragments, chimeric antibodies or other antigen-specific antibody fragments.

As used herein "biochemical marker" or just "marker", includes a protein, protein fragment, polypeptide, domain structure, peptide or otherwise proteolytically processed protein, representing changes within a specific tissue, which becomes detectable in relation to such changes.

As used herein, "nitrated epitope", includes a site within an antigen containing a nitrophenylalanine, nitrotyrosine or nitrotryptophan residue, where the epitope recognized by an antibody constitutes the nitrated residue and enough adjacent amino acid residues to gain protein specificity for the antibody.

As used herein "two independent epitopes", means two sites within the same protein, polypeptide, or peptide recognized by two different antibodies which preferably can bind their respective epitopes simultaneously. Preferably one of the sites is or contains a single nitrated aromatic amino acid residue.

As used herein, "nitrated aromatic amino acid residue", means a phenylalanine, tyrosine or tryptophan residue situated in a protein or peptide, where the aromatic ring of the amino acid residue has been modified by covalent attachment (substitution) of a $NO_2$-group.

As used herein, "nitrophenylalanine" means a phenylalanine residue situated in a protein or peptide, where the aromatic ring of the phenylalanine residue has been modified by covalent attachment of a $NO_2$-group.

As used herein, "nitrotryptophan", means a tryptophan residue situated in a protein or peptide, where the aromatic ring of the tryptophan residue has been modified by covalent attachment of a $NO_2$-group.

As used herein, "nitrotyrosine", means a tyrosine or phenylanaline residue situated in a protein or peptide, where the aromatic ring of the tyrosine has been modified by covalent attachment of a $NO_2$-group or the aromatic ring of the phenylalanine residue has been modified by combined covalent attachment of an OH-group at position 4 and a $NO_2$-group in one of the remaining positions.

As used herein, "Tyr:$NO_2$", means nitrotyrosine. The preferred position of the nitro-group is adjacent to the hydroxyl-group, for example as shown in Formula I.

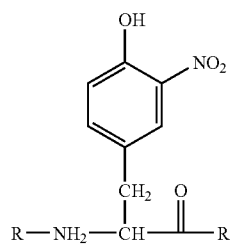

Formula 5

In one embodiment of the present invention a protein, peptide or fragment thereof containing a nitrated aromatic amino acid residue is detected by means of identification, in which the identification relies on detection of the nitrated aromatic residue, in combination with a specific amino acid sequence. The nitration of the aromatic amino acid has arisen as a result of oxidative damage, preferably connected to an inflammatory condition.

In one preferred embodiment of the present invention the nitrated aromatic amino acids to be measured are nitrotyrosine and/or nitrotryptophan residues. Most preferred are nitrotyrosine residues, which can either be generated through the nitration of a tyrosine residue, or through the combined hydroxylation and nitration of a phenylalanine residue.

In pathological processes involving oxidative damage, the degree of nitrated proteins can be used to assess the severity of this damage.

In one embodiment of the present invention this is assessed by generating an index of oxidative damage by measuring a nitrated residue in conjunction with its surrounding sequence of a protein, peptide or fragment thereof containing a nitrated aromatic amino acid residue versus the equivalent non-nitrated protein, peptide or fragment thereof, with the exception that a nitrotyrosine may be a phenylalanine in the non-nitrated peptide.

Another embodiment of the present invention includes its application for in-vitro diagnosis or assessment of severity of a disease connected to an oxidative pathology and/or inflammatory condition. Such diseases could be, but is not limited to, arteriosclerosis, Alzheimer's, asthma, Chrons disease, Parkinson's disease, cancer, cataractogenisis, diabetes, bronchopulmonary dysplasia, multiple sclerosis, muscular dystrophy, inflammatory bowel diseases, psoriasis, systemic lupus erythematosus, osteoarthritis or rheumatoid arthritis Inflammation of joint tissues is seen in conjunction with arthritic diseases such as RA and OA or as a result of an acute joint injury. This inflammatory condition is very often connected to a catabolic process within the tissue, leading to its gradual degradation. Such catabolic processes within a tissue, releases proteins, peptides or fragments thereof to numerous body fluids, like the synovial fluid, blood, serum or urine. Such molecules can be utilized as biochemical marker(s) for joint tissue degradation/catabolism. Protein or protein fragments derived from the cartilage matrix or subchondral bone, containing at least one tyrosine, phenylalanine or tryptophan residue are more likely to become nitrated upon the inflammatory increase in NO production as seen in OA and RA. Measuring nitrated versus non-nitrated catabolic markers enables the correlation between degradation and inflammation. This principle can also be applied to markers for gut inflammatory diseases or other diseases where oxidative $NO_2$-modifications occur, such as in arteriosclerosis, cancer, Alzheimer's or Parkinson's disease.

In one embodiment of the present invention the nitrated aromatic residues have arisen as a result of an inflammatory condition in a joint tissue is situated in a protein, peptide or fragment thereof derived from the extra cellular matrix or cartilage, joint synovium or subchondral bone, which can be measured in order to monitor the catabolic process in the tissue.

In one preferred embodiment, the protein or fragment thereof, which is monitored, constitutes a marker of cartilage degradation associated with an inflammatory joint disease. The nitrated form versus the non-nitrated form of such a cartilage matrix derived marker is measured generating an index of inflammation.

Proteins or fragments thereof, which can be nitrated and act as markers of interest include, but are not limited to, collagen types I, II, III, VI, IX or XI, aggrecan, cartilage link protein, cartilage oligomeric matrix protein, cartilage intermediate layer protein.

A preferred marker protein is collagen type II. Collagen type II contains two tyrosine's, which can be nitrated upon oxidative damage. The first sequence HRGYPGLDG (His-Arg-Gly-Tyr-Pro-Gly-Leu-Asp-Gly) (SEQ ID NO: 1) is localised in the triple helical region while the second sequence LQYMRA (Leu-Gln-Tyr-Met-Arg-Ala) (SEQ ID NO: 2) is located in the non-helical domain at the C-telopeptide. The amino acids sequences including the tyrosine residues are specific for type II collagen and can be employed as specific biochemical markers of catabolic processes in the cartilage tissue.

A preferred embodiment is the detection of the nitrated type II collagen marker versus the equivalent non-nitrated type II collagen marker providing an index of the oxidative damage and/or the inflammatory condition of the cartilage tissue in associated with the metabolic condition of the same tissue. The principle of this method also applies to other tissue specific markers originating from oxidative damaged tissues undergoing metabolic changes at the same time.

Especially for monitoring the results of a treatment this is of importance, as some forms of treatment might influence the catabolic process whereas others might influence the inflammatory state. This more differentiated assessment of the disease obtained by application of the present invention will enable therapeutic interventions to be targeted to individual patients.

The detection of a nitrated aromatic amino acid residue in combination with a sequence located within a specific protein, peptide or fragment thereof can be performed in numerous ways, such as, but not limited to, HPLC, mass spectroscopy, iso-electric focusing, sequencing or immunoassays.

One preferred method of detection is the use of an immunoassay, utilizing an antibody, which specifically binds at least one nitrated aromatic amino acid residue in conjunction with the surrounding amino acid sequence of a specific protein (nitrated epitope). Assay forms in which such an antibody can be applied include, but not limited to, ELISA, microarray, RIA, FACS, Western blotting, immunoaffinity chromatography, and immunohistochemistry.

Another method of detection is a sandwich immunoassay, utilizing an antibody, which specifically recognizes a nitrated aromatic amino acid residue independent of the surrounding sequence and a second antibody, which recognizes a specific amino acid sequence located within the same protein, peptide or a fragment thereof as the nitrated amino acid residue. The second antibody can very well be a polyclonal antibody with specificity towards a specific protein e.g. collagen type II, where the actual epitope has not been identified.

The most preferred method for monitoring a pathological process involving oxidative damage and/or an inflammatory condition in association with metabolic changes utilizes the generation of an index as described above. More specifically such an index is generated by contacting an antibody, which specifically binds a nitrated epitope, with a biological sample. Upon reaction with the first antibody, the antibody-peptide conjugates can be detected by different affinity/visualization or isolation methods. If appropriate, a second antibody, which specifically binds an equivalent non-nitosylated amino acid sequence as the first antibody, is contacted with an aliquot of the same biological sample as the first antibody, or the remnants (supernatant) resulting from an isolation of the first antibody-peptide conjugate. The ratio between nitrated and non-nitrated peptide and/or protein in the biological sample is determined. Methods of determination are well known in the art, for example ELISA, microarray, RIA, FACS, immunoaffinity chromatography, and immunohistochemistry. If applying other methods than chromatography, it is important that the two antibodies are labelled in a manner that enables differentiation between them. This could be different fluoresce (e.g. red, green, yellow), enzymatic label vs. radioactive label and so forth. An index of oxidative damage and/or inflammation in association with the metabolic condition of the tissue from where the specific protein originates can be provided by evaluating ratios from a patient in relation to ratios from healthy individuals.

In situations where a tissue sample is used for monitoring of pathological processes in joint tissue, there is a strong likelihood that denatured helical collagen domains, resulting from catabolic processes within the tissue, might be retained in the tissue by cross-linking and fibrillar packaging. To address this problem, the biological sample is first contacted with an enzyme having the ability to selectively cleave unwound (non-helical) collagens without cleaving the His-Arg-Gly-Tyr-Pro-Gly-Leu-Asp-Gly (SEQ ID NO: 1) and/or the Leu-Gln-Tyr-Met-Arg-Ala (SEQ ID NO: 2) epitope. Such enzymes could be, but is not limited to, trypsin or chymotrypsin, which are unable to cleave wound (native) collagen within the α-helix. The fragments of unwound collagen are then extracted from the biological sample to produce an extract of unwound collagen fragments. This extract can then be assayed as mentioned in the above.

Antibodies with the properties described above are raised against a peptide constituting a nitrated epitope. The peptide is used as an antigen for immunisation. The peptide is emulsified in an adjuvant medium, preferably incomplete Freund's adjuvant and injected subcutaneously or into the peritoneal cavity of a mammalian host, preferably a rodent most preferred rabbits, even more preferred BalbC mice. To enhance immunogenic properties of the antigenic peptide it can be coupled to a carrier protein before emulsified in an adjuvant medium. Useful carriers are proteins such as keyhole limpet hemocyanin (KLH), edestin, thyrogloboloin, albumins, such as bovine or human serum albumin (BSA or HSA), tetanus toxoid, and cholera toxoid, polyaminoacids, such as poly-(D-lysine-D-glutamic acid). Booster injections may be given at regular intervals until an immune response is obtained, the last injection may be given intravenously to ensure maximal B-cell stimulation.

Antisera will be screened for their ability to bind the desired epitope and their amount of cross reactivity to the non-nitrated epitope. Antisera from the most promising hosts may be used in their crude form or purified.

Monoclonal antibodies may be prepared from the immunised mice with the highest antibody titre, by fusing lymphocytes isolated from the spleen of these mice with a myeloma cell line. The generated hybridoma clones are screened for their ability to produce antibodies, which recognize the desired epitope. Cell lines can be established for production and purification of monoclonal antibodies.

Methods for polyclonal and monoclonal antibody production are well known in the art and other methods than the described can also be utilized.

In one aspect of the present invention the synthetic peptide for antibody and cell line generation as described above is $(Xaa)m$-His-Arg-Gly-Tyr:$N_{O2}$-Pro-Gly-$(Xaa)n$ (SEQ ID NO: 3), wherein Xaa denote any amino acid or derivatives thereof and m and n are independent integers e.g. from 0 to 10.

In one preferred embodiment of the present invention the synthetic peptide for antibody and cell line generation as described above is $(Xaa)m$-His-Arg-Gly-Tyr:$NO_2$-Pro-Gly-Leu-Asp-Gly-$(Xaa)n$(SEQ ID NO: 4), wherein Xaa denote any amino acid or derivatives thereof and m and n are independent integers e.g. from 0 to 10.

In another preferred embodiment the synthetic peptides for antibody and cell line generation as described above has the form $(Xaa)m$-Leu-Gln-Tyr:$NO_2$-Met-Arg-Ala-$(Xaa)n$(SEQ ID NO: 5), wherein Xaa denote any amino acid or derivatives thereof and m and n are independent integers e.g. from 0 to 10.

With the exception that a nitrotyrosine may be derived from a phenylalanine in the non-nitrated peptide, the second antibodies utilized in the present invention are generated using the same or similar techniques as for the preparation of the nitrosyl binding antibodies.

One embodiment of the present invention constitutes the development of a diagnostic kit for use in detection and monitoring of oxidative damage and/or an inflammatory condition. This includes an antibody recognizing a nitrated epitope, preferably utilizing an antibody of the present invention, either alone or in combination with a second antibody with specificity towards the equivalent non-nitrated sequence, enabling a simultaneous assessment of tissue metabolism and oxidative damage. The kit can be applied on mammalian body fluids or extracts of cells or tissues, preferably derived from humans. For competition detections a peptide of 6 to 20 amino acids, in which a succession of amino acids is equivalent to the binding epitope for one of said antibodies, might be supplied either in a labelled or non labelled form. The antibodies may be labelled by joining them, either covalently or non-covalently, with a reporter molecule. Suitable reporter molecules or labels, which may be used for ease of detection, include radioisotopes, enzymes, fluorescent, chemiluminescent, or chromogenic agents as well as substrates, cofactors, inhibitors, magnetic particles, and the like. One of the non-labelled antibodies or a peptide of the kit might be immobilised, preferably on a solid surface like a micro-titter plate, possibly by conjugation to a suitable protein carrier like BSA.

In a preferred embodiment the first antibody in the kit described above recognize the nitrosylated collagen type II sequences previously described, and the second antibody recognizes the equivalent non-nitrated sequence.

BRIEF DESCRIPTION OF THE DRAWINGS

The invention will be further described and illustrated with reference to the accompanying drawings, in which.

DETAILED DESCRIPTION OF THE INVENTION

EXAMPLES

Example 1

Collagen Type II Immunoassay

Antisera:

A sequence of nine amino acids (His-Arg-Gly-Tyr:NO$_2$-Pro-Gly-Leu-Asp-Gly) (SEQ ID NO: 6) derived from the triple helical region of type II collagen [(α1) II]and a second sequence of six amino acids Leu-Gln-Tyr:NO$_2$-Met-Arg-Ala (SEQ ID NO: 7) derived from the C-telopeptide of type II collagen were synthesized using standard Fmoc solid-phase peptide synthesis (HBTU/HOBt protocol) (Chan, W. C. and White, P. D., 2000).

The amino acids sequence was conjugated to thyroglobulin by a carbodiimide procedure (Soinila et al 1992).

Rabbits were injected intraperitoneally with 1 ml of the conjugate emulsified in complete Freund's adjuvant. The conjugate and the adjuvant were mixed in equal volumes. Injections were repeated four times every month with a similar amount of conjugate in incomplete Freund's adjuvant. Ten days after the last injection, the rabbits were sacrificed for the final bleeding. Blood were collected and centrifuged for 10 minutes at 1500×g at 4° C. The supernatants were stored at −20° C.

The following examples will concentrate on antisera achieved from immunisation with the His-Arg-Gly-Tyr:NO$_2$-Pro-Gly-Leu-Asp-Gly (SEQ ID NO: 6) peptide. All examples can be performed in similar ways for the Leu-Gln-Tyr:NO$_2$-Met-Arg-Ala (SEQ ID NO: 7) peptide.

Six antisera, identified as Coll2-1:NO2 D35, D36, D37, D38 D39 and D40, were obtained and their specificity were tested with the competitive inhibitions His-Arg-Gly-Tyr (NO$_2$)-Pro-Gly-Leu-Asp-Gly (SEQ ID NO: 6), His-Arg-Gly-Tyr-Pro-Gly-Leu-Asp-Gly (SEQ ID NO: 1), type II nitrated collagen, native type II collagen, type I nitrated collagen I, type I collagen, nitrated BSA and BSA.

Figure 1:
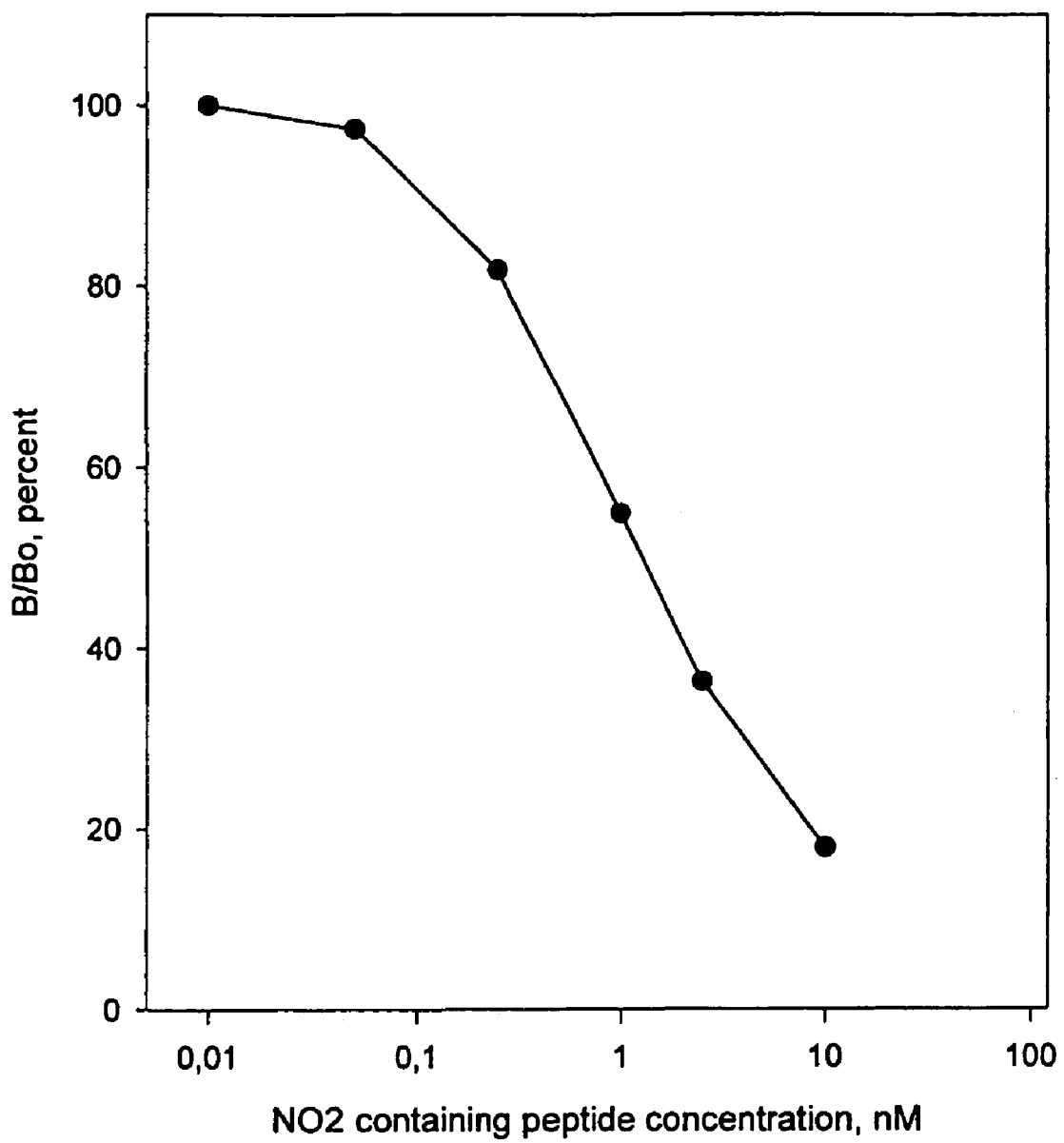
FIG. 1 shows a standard curve for nitrated collagen type II immunoassay in a semi-logarithmic plot. The concentration of free antigen is in nM. B/Bo represents the ratio between antibody bound to coated antigen in the presence of free antigen (B) or in the absence of free antigen (Bo) and is given in percentage.
Figure 2:
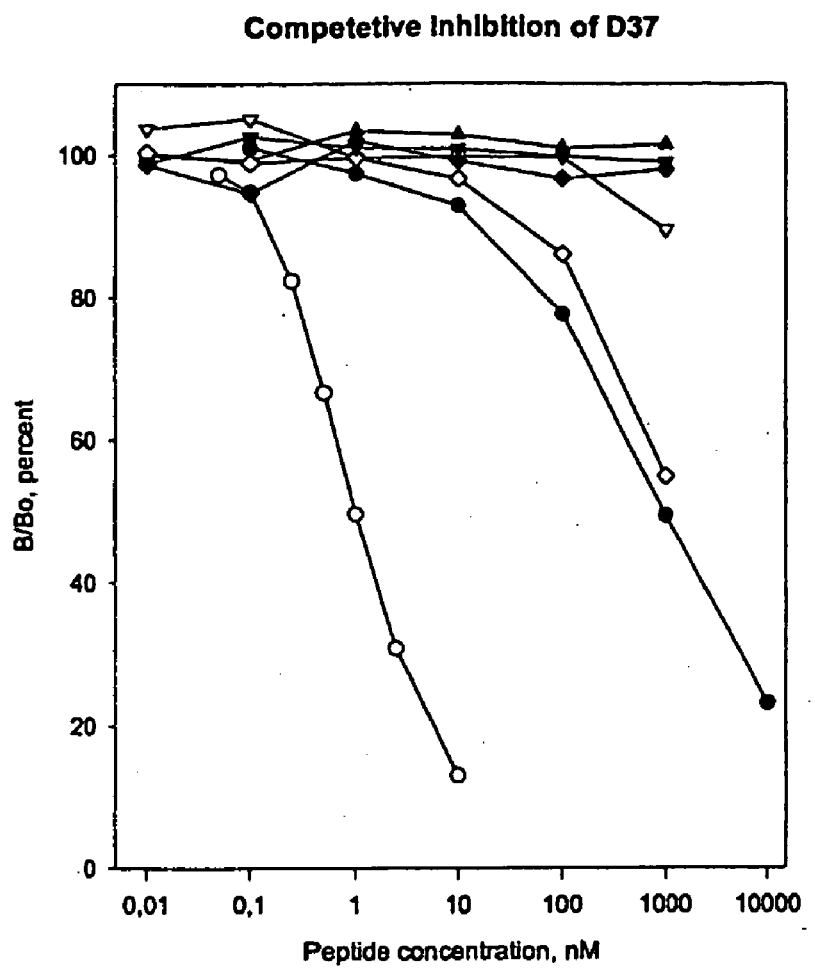
FIG. 2 shows competitive inhibition of antiserum D37 binding to His-Arg-Gly-Tyr:NO$_2$-Pro-Gly-Leu-Asp-Gly (SEQ ID NO: 6) coated plates using His-Arg-Gly-Tyr:NO$_2$-Pro-Gly-Leu-Asp-Gly (SEQ ID NO: 6) (O), His-Arg-Gly-Tyr-Pro-Gly-Leu-Asp-Gly (SEQ ID NO: 1) (●), native type II collagen (♦), nitrated type II collagen (◊), type I collagen ( ), BSA ( ) and nitrated BSA (∇) as competitors. B/Bo represents the ratio between antibody bound to coated antigen in the presence of competitor antigen (B) or in the absence of competitor antigen (Bo) and is given in percentage.

Competitive ELISA:

A competitive immunoassay was developed to quantify breakdown products of nitrated type II collagen containing following sequence His-Arg-Gly-Tyr:NO$_2$-Pro-Gly-Leu-Asp-Gly (SEQ ID NO: 6). Synthetic His-Arg-Gly-Tyr:NO$_2$-Pro-Gly-Leu-Asp-Gly (SEQ ID NO: 6) peptides were biotinylated and incubated at 1.25 ng/ml on streptavidie coated plates (Nunc, Denmark) for 1 hour at room temperature. Fifty µl of calibrators (to generate a standard curve) or unknown samples, diluted in Ultroser G (Gibco) were added to separate wells. Hundred µl antiserum (see above) diluted {fraction (1/125000)} was added to each well. Samples were mixed by rotating the plate and incubated 1 hour at room temperature. After three successive washings with washing buffer (Tris 25 mM, NaCl 50 mM pH 7.3), 100 µl of horseradish peroxidase-conjugated goat antibodies to rabbit IgG (Biosource, Belgium) were added to each well and incubated 1 hour at room temperature. After washing, 100 µl of freshly prepared enzyme substrate (TMB, Biosource, Belgium) were added to each well. After 15 minutes incubation, the reaction was stopped with 100 µl 4M H$_3$PO$_4$. The coloration was read with a microplate reader (Labsystem iEMS Reader MF, Finland) at 450 nm and corrected for absorbance at 620 nm. A standard curve was constructed on a log-linear graph by plotting the B/Bo of 6 calibrators (10 to 0.01 nM) (FIG. 1). The concentration of HIS-ARG-GLY-TYR:NO2-PRO-GLY-LEU-ASP-GLY (SEQ ID NO: 6) containing peptides in the samples, were determined by interpolation on the calibration curve.

Detection Limit

The detection limit of the assay described in example 1, is calculated as the mean (M) Bo value of 21 determinations of standard A minus 3 times the standard derivation (SD) of Bo ($M_A-3*SD_A$). For Coll2-1:NO2 D37 the detection limit was 25 pM.

Example 2

Characterisation of Antisera Coll2-1:NO2 D37-40

Specificity

The antisera produced, were tested for their specificity for His-Arg-Gly-Tyr:NO$_2$-Pro-Gly-Leu-Asp-Gly (SEQ ID NO: 6), by use of the immunoassay described in example 1. To test for specificity His-Arg-Gly-Tyr:NO$_2$-Pro-Gly-Leu-Asp-Gly (SEQ ID NO: 6), His-Arg-Gly-Tyr-Pro-Gly-Leu-Asp-Gly (SEQ ID NO: 1) peptide, type II nitrated collagen, native type II collagen, type I nitrated collagen, type I collagen, nitrated BSA and BSA.

Native type II collagen, type I collagen, nitrated collagen type I, nitrated BSA and BSA, were not able to compete with the coated His-Arg-Gly-Tyr:NO$_2$-Pro-Gly-Leu-Asp-Gly (SEQ ID NO: 6) peptide in the applied concentrations, whereas the antiserum showed weak affinity to the non-Nitrated His-Arg-Gly-Tyr-Pro-Gly-Leu-Asp-Gly sequence (SEQ ID NO: 1) and nitrated collagen type II and strong affinity to the His-Arg-Gly-Tyr:NO$_2$-Pro-Gly-Leu-Asp-Gly (SEQ ID NO: 6) sequence. A lack of binding affinity has also been demonstrated with L-nitrotyrosine.

Example 3

Coll2-1(NO2) Levels are Elevated in Animal Models of Inflammatory Arthritis

A number of animal models have been established to study inflammatory arthritis. These models generally reflect the human disease, by having joint inflammation and tissue destruction. Significant up-regulation of inflammatory cytokines and NO levels have been detected. Thus, nitrosylation of tyrosine residues is likely to occur in these situations. By this example, it was demonstrated that sera samples of normal rats and mice could be measured in the Col2-1 (NO2) assay described in example 1.

One of the most commonly employed animal models of RA is the Lewis-rat Collagen Induced Arthritis (CIA) animal model. In this model, joint inflammation is induced by immunization with collagen type II which provoke a severe inflammatory response to joint cartilage apparent as paw joint swelling and subsequent destruction of joints when histological analysis is performed. Arthritis was monitored by macroscopic scoring of swelling and redness of the paws. Cartilage and bone erosion was monitored by quantifying urinary levels of CartiLaps and serum levels of RatLaps, two biochemical markers of cartilage and bone resorption. These assays were performed as specified by the manufacturer (Nordic Bioscience Diagnostics, Herlev, Denmark).

The study cohort comprised 21 female Lewis rats which are ovarectomized (OVX). At baseline, the weight was determined and the animals were anesthesised for the OVX procedure. After induction of general anesthesia with Hypnorm-Dormicum (1 part Hypnorm®+1 part Dormicum®+2 part sterile de-ionised water, dose 0.15-0.2 ml/100 g body weight), a standard OVX was performed. The weight of the animals was determined on a weekly basis throughout the study period. For measurements of bone and cartilage markers urine samples were obtained by either placing the animals in a metabolic cage for 30-60 min and awaiting spontaneous urination or by gently rubbing the belly of the animal, i.e. forced urination and by obtaining blood samples as eyeblood. At study termination, the knees were isolated and the articular cartilage was analyzed for erosion histologically. The rats were immunized with collagen type II 1 week after OVX to induce inflammatory arthritis. Each rat was immunized with 150 µg bovine collagen type II emulsified in Incomplete Freunds Adjuvant. The paws of the rats were scored daily from day 11 by visual observation of the paws. Each paw is scored on a scale 0-4 and the score for the four paws are added. If the combined arthritis score reached a score of 10 for a given animal or if the animal developed very severe arthritis in one paw or had CIA for more that 16 days, the animal was sacrificed for ethical considerations, as more severe arthritis is associated with significant pain and discomfort. The remainder of the animals were maintained for 27 days after OVX before being terminated.

Figure 3:
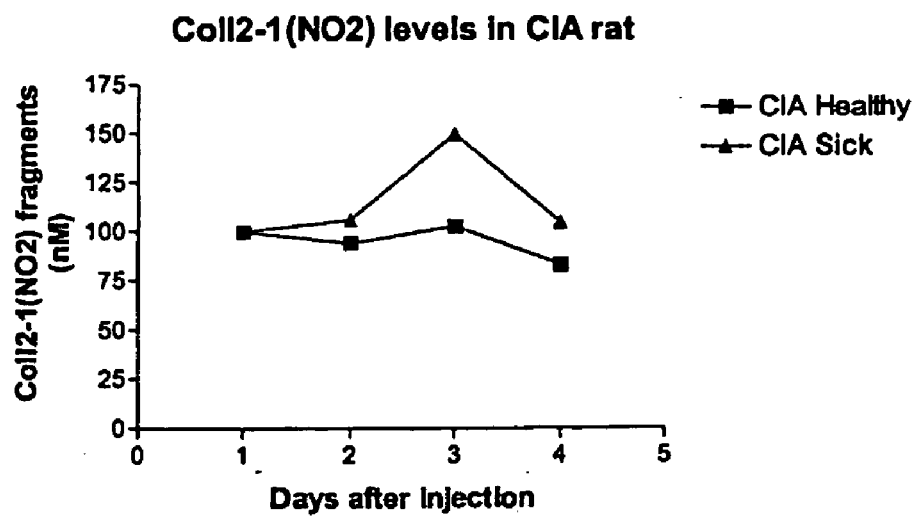
FIG. 3 shows results from Example 3 and gives the level of Coll2-1(NO2) fragments in serum from Lewis rats immunized with bovine collagen type II. The graphs depict the levels of the markers in animals which did not develop disease (CIA healthy) and the animals that developed inflammatory arthritis (CIA sick)

The Coll2-1 (NO2) level in the serum and the presence of external signs of arthritis had a very good correlation (FIG. 3). The levels of Coll2-1(NO2) were significantly elevated in the rats which developed inflammatory arthritis (sick) whereas animals which did not develop disease showed significantly lower levels of Col2-1(NO2). Moreover, the level of collagen fragments increased before the appearance of severe arthritis symptoms implying that Coll2-1(NO2) is a predictive biomarker for inflammation induced cartilage erosion.

Example 4

Human Articular Cartilage Explants Produce Coll2-1 (NO2) in vitro

Figure 4:
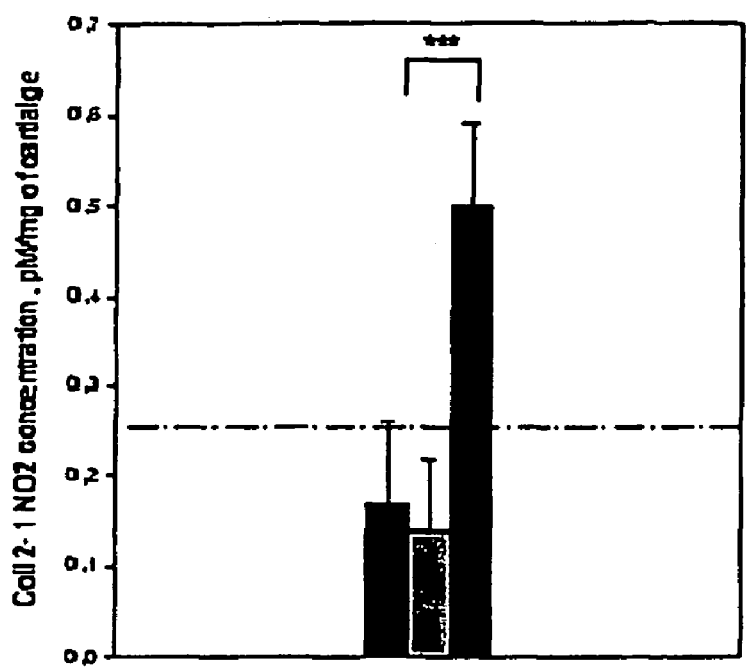
FIG. 4 shows results from Example 4 demonstrating that human articular cartilage explants produce Coll2-1(NO2) in vitro. From left to right the bars show results from a control, upon stimulation with IL1, oncostatin and plasminogen, and upon stimulation with IL1, oncostatin, plasminogen and the plasminogen activator aminophenyl mercuric acetate (APMA)

Articular cartilage explants are commonly used as an in vitro system to assess cartilage metabolism. Articular cartilage was obtained from adult human patients undergoing joint replacement surgery and the cartilage was excised either as cylindrical plugs (5-30 mg) or as slices (20-30 mg). The explants were cultured in 96-well plates in 200 mL serum free DMEM medium, in the presence of recombinant human IL-1α5 ng/mL (Sigma, St. Louis, USA), Oncostatin M 50 ng/mL (Sigma, St. Louis, USA) and human plasminogen 10 µg/mL (Sigma, St. Louis, USA). Plasminogen is a physiological MMP activator that induces collagen type II degradation. Furthermore the MMP activator APMA (aminophenyl mercuric acetate, SIGMA, St. Louis, USA) was added as indicated in FIG. 4. The conditioned medium was harvested at various time points for measurement of Coll2-1(NO2) This example shows how the cytokines IL1 and oncostatin (OSM) influence the release of Coll2-1(NO2) in the conditioned medium from cartilage explants.

It was demonstrated that addition of IL1, oncostatin and plasminogen had no influence on cartilage degradation. However a significant level of Coll2-1(NO2) could be detected in conditioned medium of cartilage explants when the plasminogen activator APMA was also added to the medium (FIG. 4). This observation links the release of the Col2-1(NO2) marker from articular cartilage to collagenolytic activity in the matrix, and demonstrates that the marker reflects catabolic processes in the tissue.

Example 5

Physiological Levels of Coll 2-1(NO2) in Healthy Men and Women

To establish reference values for Coll 2-1 (NO2), sera were collected from 242 healthy ambulatory subjects attending a blood donor centre in Liege, Belgium. None of the study subjects had any evidence of arthritis or other inflammatory disease. None was currently taking any medication known to modify arthritic disease or influence joint metabolism. This group was composed by 170 men and 72 women, aged from 20 to 65 years (mean: 42.8±1.4 years). The mean age of women was 42.7±1.0 years old and the mean age of men was 42.8±1.4 years old.

Figure 5:
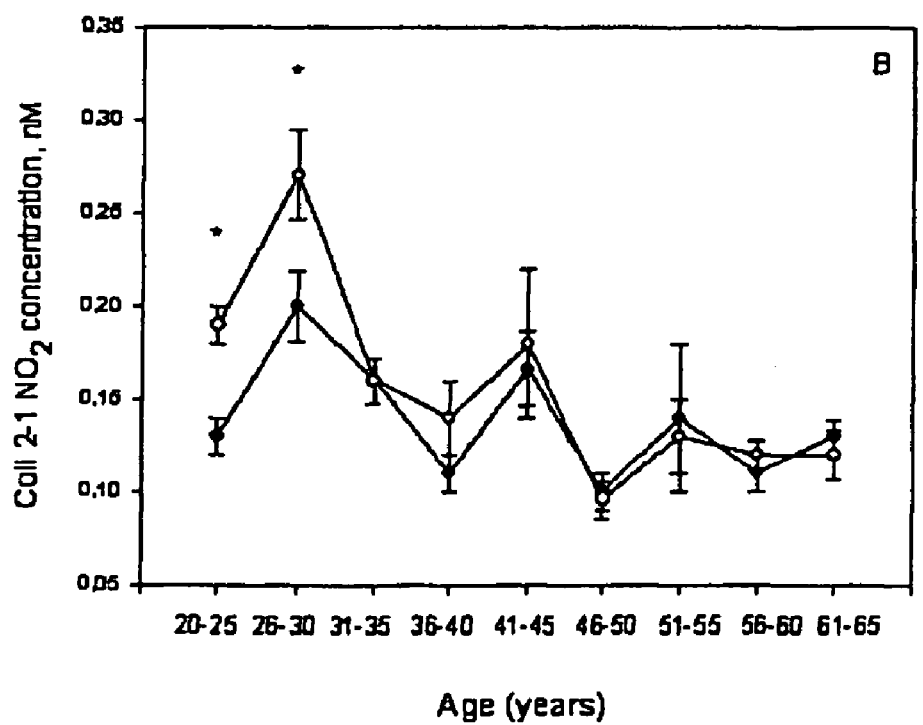
FIG. 5 shows results obtained in Example 5 giving the physiological variation of Coll2-1 (NO2) fragment levels in serum according to age range and sex (men plain black diamonds, and women white diamonds)

When the population was stratified by age in 5 years brackets, Coll 2-1 (NO2) serum levels did not vary significantly in the investigated age interval (20-65 years) (FIG. 5). The comparison of peptide levels by sex showed that up to 45 years of age, Coll 2-1 (NO2) concentration was higher in women than in men but the difference was only significant for the subclasses 20-25 and 26-31 years old (figure X+3). However, when subjects aged from 46 to 55 years corresponding to the early postmenopausal women were removed, Coll 2-1 (NO2) level was higher in pre-menopausal women than in postmenopausal women.

Figure 6:
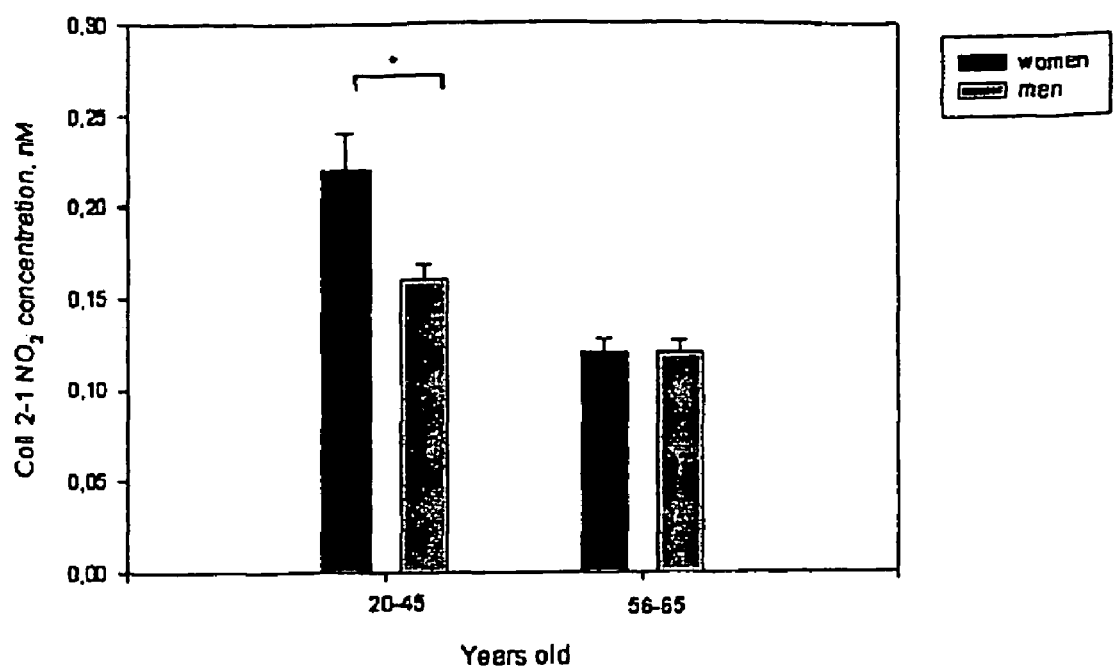
FIG. 6 shows results obtained in Example 5 giving the physiological variation of Coll2-1(NO2) fragment levels in serum in men and women subdivided in two large age groups.

Coll2-1(NO2) level is higher in young individuals (pre-menopausal) than in older individuals (FIG. 6). The level of these fragments is identical for both men and women in the range of 56-65 years old whereas pre-menopausal women showed significantly higher levels of the marker compared to men and postmenopausal women. This observation corresponds well with the established link between estrogen levels and nitric oxide. Estrogen up-regulates production of inducible nitric oxide synthetase (iNOS) and thus levels of nitric oxide, which in turn is responsible for generation of nitro tyrosine modified proteins as quantified in the Col2-1(NO2) assay. Hence the elevated levels of this marker measured in the premenopausal women establishes a link between estrogen levels and nitrosylation.

Example 6

RA Patients have More Elevated Coll2-l(NO2) Levels than OA Patients

An important clinical issue is whether levels of the Col2-1(NO2) marker are elevated in arthritis and are associated with the inflammatory process seen in RA. To study this, serum samples were obtaind from a cross-sectional panel of arthritis patients comprising 10 OA patients (4 women and 6 men aged over 45 years) who were candidates for arthroscopy. Arthroscopy was performed for diagnosis and/or shaving of the meniscus and cartilage lesions. Sera were collected 24 hours prior surgery. These subjects had no radiological signs of OA but all had cartilage lesions identified by arthroscopy. All subjects had a normal leukocytosis and a C-reactive protein (CRP) level inferior to 5 mg/L. Furthermore, these patients did not take any nonsteroidal anti-inflammatory drugs during the year before the intervention.

Coll 2-1 (NO2) concentration were also measured in serum samples of 14 patients with early RA. At the sampling time, these patients had not received any medication, and all had a C-reactive protein level above 5 mg/L.

Figure 7:
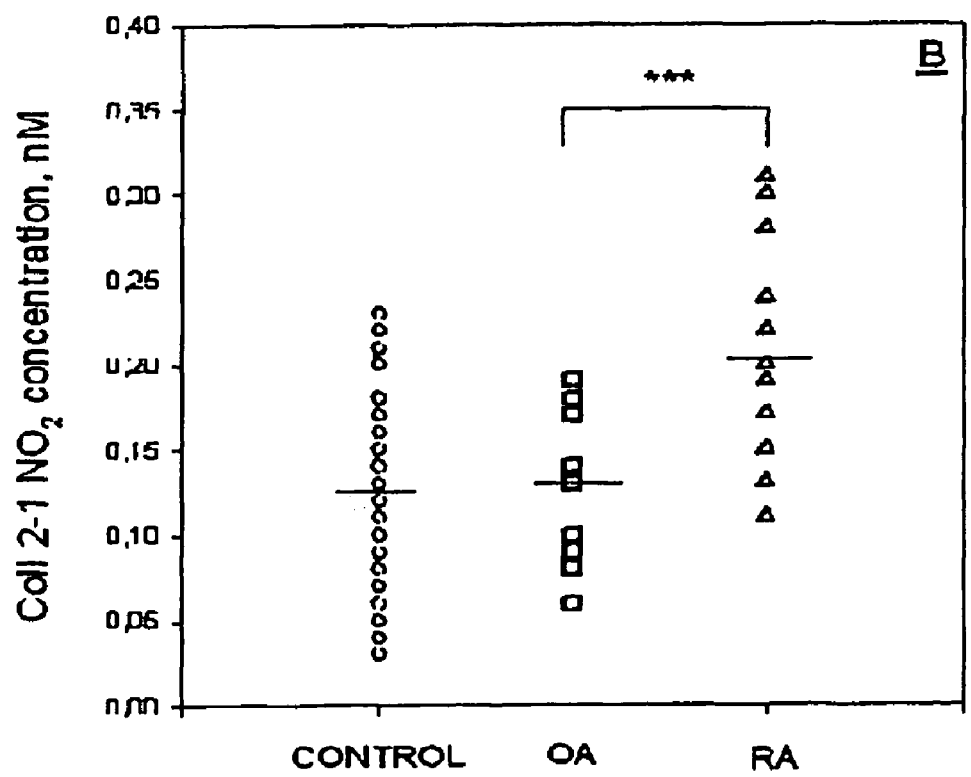
FIG. 7 shows results obtained in Example 6 demonstrating that RA patients have more elevated Coll2-1 (NO2) levels than OA patients.

When comparing the levels of Coll2-1(NO2) in these cohorts it was apparent that the RA patients where inflammation of the joint tissue is a significant element of the disease had significantly higher levels of the marker than OA patients or controls (FIG. 7). This observation associated the Coll2-1 (NO2) production directly to inflammation associated cartilage degradation in inflammatory arthritis.

Example 7

Development of an Assay Specific for a Nitrosylated Collagen Type II Epitope Derived from the C-Telopeptide Region (Coll2-2(NO2) ELISA)

Reagents and Buffers for Immunoassays

The coating buffer was 0.08 M NaHCO$_3$ pH 9.6. The saturation buffer was composed of 1.5 mM KH$_2$PO$_4$, 8 mM Na$_2$HPO$_4$, 2 mM KCl, 138 mM NaCl, 5 g/L bovine serum albumin (BSA), 53 g/L lactose monohydrate pH 7.2. The washing buffer was a solution of 25 mM Tris, 50 mM NaCl pH 7.3. The standard curve and the dilution of samples, when it was necessary, were realized in 50 mM Tris, 138 mM NaCl, 7 g/L BSA, 1 ml/L Tween 20 pH 8.0.

The dilutions of the antisera (1/80 000) and of the second antibody 1/5000) were done in Na$_2$HPO$_4$ 10 mM, KH$_2$PO$_4$ 1.5 mM, KCl 2 mM, NaCl 150 mM, EDTA 25 mM, BSA 1% Tween 0.1% pH 7.4.

Immunization

Rabbits were injected intra-peritoneally with 1 ml of the conjugated peptides (0.5 mg/ml) emulsified in complete Freund's adjuvant. The conjugate and the adjuvant were mixed in equal volumes. Injections were repeated four times every month using the same peptide concentration that those of the first injection in incomplete Freund's adjuvant. Ten days after the last injection, the rabbits were sacrificed. Blood was collected and centrifuged for 10 mm at 2500 rpm at 40° C. The supernatant was kept and stored at −200° C. At each bleeding, antisera were screened by titration experiment for the presence of anti-GGGLQY(NO$_2$)MRA (SEQ ID NO: 8) antibody. The antisera with the highest titers were selected for the following experiments.

Specificity

Figure 8:
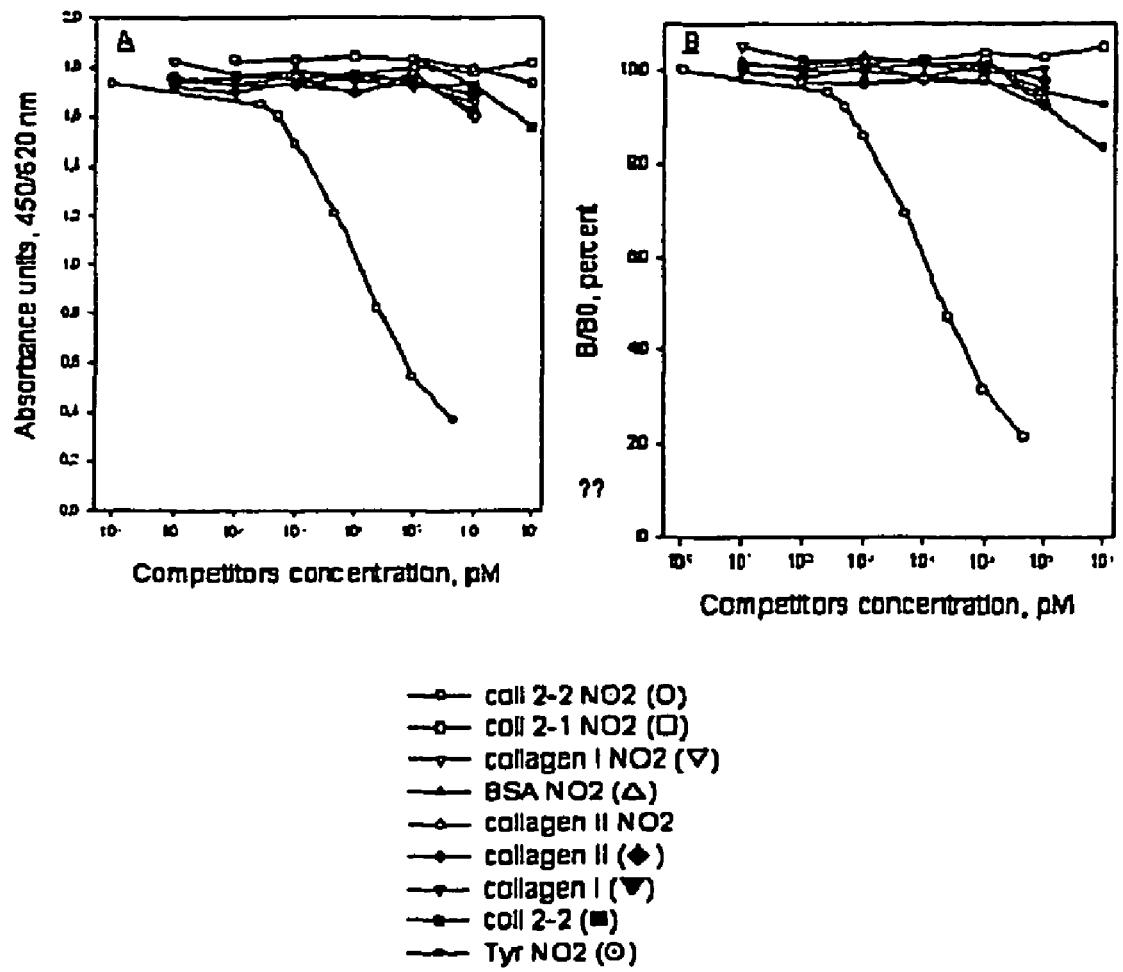
FIG. 8 provides results obtained in Example 7 showing levels of cross reactivity of antibody anti-Coll2-2 (NO2) (antiserum D33).

D33 antibody is highly specific for nitrosylated Coll2-2 fragment and does not react with the same fragment non-nitrosylated Coll2-2 or with any other fragment slightly similar in the sequence (Coll2-1) or completely different sequences (BSA NO2). The figured showed also that the chosen sequence of Coll2-2 against which D33 was raised cannot be recognized when it is still "included" in the full length protein (Coll II (NO2)). The nitrosylated sequence is recognized only in the form of free fragments (FIG. 8).

Assay Technical Performance

CV intra-assay: In order to address the question of correct and reproducible results measured in this assay intra-assay CV was evaluated by measurement of the same urine samples in different emplacement in the same plate.

TABLE 1

Evaluation of intra-assay CV (%) of Coll2-2 NO2) assay.

| | Coll 2-2 (NO2) concentration (Mean ± SD, nM) | CV intra-assay (%) |
|---|---|---|
| Urine 1 | 1.56 ± 0.15 | 9.1 |
| Urine 2 | 2.86 ± 0.26 | 9.1 |

The intra-assay showed that the samples could be measured in a good reproducible manner (Good standard variation of samples mean concentration of Coll2-2(NO2) fragments). The CV on samples measurement for both samples used here were below 10% witnessing also of the assay precision.

Recovery: The certainty of Coll2-2 measurement is assessed by successive dilution of the samples. The dilution of the samples allows us to evaluate the recovery (expressed in %). The table below summarize the evaluated recoveries for two urine samples. The assay performed correctly (see table below).

TABLE 2

Recovery of Coll2-2 (NO2) fragments in two urine samples after dilution of respectively ½; ¼ and ⅛.

| | Coll 2-2 (NO2) concentration, nM | Recovery (%) |
|---|---|---|
| Urine samples 1 | | |
| Undiluted | 9.26 | — |
| Dil. ½ | 5.57 | 120.1 |
| Dil. ¼ | 2.26 | 106.0 |
| Dil. ⅛ | 1.42 | 122.3 |
| Urine samples 2 | | |
| Undiluted | 2.74 | — |
| Dil. ½ | 1.55 | 113.1 |
| Dil. ¼ | 0.85 | 124.1 |
| Dil. ⅛ | 0.33 | 95.6 |

REFERENCES

Chan, W. C., White, P. D., 2000 Fmoc solid-phase peptide synthesis: A practical approach, Oxford University Press, Oxford 2000.

Lin, J. K., Chen, K. J., Liu, G. Y., Chu, Y. R., Lin-Shiau, S. Y., 2000. Nitration and hydroxylation of aromatic amino acid and guanine by the air pollutant peroxyacetyl nitrate. Chem Biol Interact. 127, 219-236.

Lotz, M., 1999. The role of nitric oxide in articular cartilage damage. Rheum Dis Clin North Am 25, 269-282.

Moller, H. J., 1998. Connective tissue markers of rheumatoid arthritis. Scand J Clin Lab Invest 58, 269-278.

PCT patent application WO 96/04311, Ye Y. Z, Beckman J. S., Monoclonal Antibody to Nitrotyrosine, Methods for Diagnosis and Methods for Treatment of Disease, University Alabama Res Found (Us), 1996.

PCT patent application WO 98/29452, Chagnaud J. L., Vincendeau P., Geffard M., Veyret B., Antibodies Specifically Recognizing a Nitrated Protein, Method of Preparation, Therapeutic and Diagnostic use, Centre Nat Rech Scient (Fr), 1998

PCT patent application WO 01/38872, Christgau S., Henriksen D. B., Cloos P., Assay of Isomerised and/or Optically Inverted Proteins and Protein Fragments, Osteometer Biotech A/S (DK), 2001.

Soinila, S., Mpitsos, G. J., Soinila, J., 1992. Immunohistochemistry of enkephalins: model studies on hapten-carrier conjugates and fixation methods. J Histochem. Cytochem. 40, 231-239.

Stadtman, E. R., Levine, R. L., 2000. Protein oxidation. Ann. N. Y. Acad. Sci. 899, 191-208.

U.S. Pat. No. 5,919,634, Eyre D. R., Methods of detecting collagen type II degradation in vivo, Washington Research Foundation (Seattle, Wash.), 1999.

U.S. Pat. No. 6,132,976 Poole A. R., Hollander A. P., Billinghurst R. C., Immunoassay For the Measurement of Collagen Denaturation and Cleavage in Cartilage, Shriners Hospital for Children (Tampa, Fla.), 2000.

Wollheim, F. A., 1996. Predictors of joint damage in rheumatoid arthritis. APMIS 104, 81-93.

---

The invention claimed is:

1. A method for detecting nitrated fragments of type II collagen by immunoassay, comprising the steps of:

contacting a biological sample with an antibody that specifically binds the nitrated epitope HRGY-NO$_2$-PGLDG (SEQ ID NO: 6), wherein the amino acid residue Y-NO$_2$ therein is a nitrated tyrosine residue, and detecting binding of the antibody to unwound fragments of type II collagen in the sample that comprise said nitrated epitope;

wherein said antibody specifically binds said nitrated tyrosine residue in conjunction with the specific amino acid sequence of said nitrated epitope, and wherein said antibody does not react with the non-nitrated sequence HRGYPGLDG (SEQ ID NO: 1).

* * * * *

SEQUENCE LISTING

```
<160> NUMBER OF SEQ ID NOS: 8

<210> SEQ ID NO 1
<211> LENGTH: 9
<212> TYPE: PRT
<213> ORGANISM: Artificial sequence
<220> FEATURE:
<223> OTHER INFORMATION: Synthesized

<400> SEQUENCE: 1

His Arg Gly Tyr Pro Gly Leu Asp Gly
1               5

<210> SEQ ID NO 2
<211> LENGTH: 6
<212> TYPE: PRT
<213> ORGANISM: Artificial sequence
<220> FEATURE:
<223> OTHER INFORMATION: Synthesized

<400> SEQUENCE: 2

Leu Gln Tyr Met Arg Ala
1               5

<210> SEQ ID NO 3
<211> LENGTH: 26
<212> TYPE: PRT
<213> ORGANISM: Artificial sequence
<220> FEATURE:
<221> NAME/KEY: VARIANT
<222> LOCATION: (1)...(10) (17)...(26)
<223> OTHER INFORMATION: Synthesized; Xaa at poisition No. 14 is a nitrated
      tyrosine (Tyr:No2); Xaa at positions 1 to 10 and 17 to 26 denotes
      any amino acid or derivatives thereof and can be
      present or absent

<400> SEQUENCE: 3

Xaa Xaa Xaa Xaa Xaa Xaa Xaa Xaa Xaa Xaa His Arg Gly Xaa Pro Gly
1               5                   10                  15

Xaa Xaa Xaa Xaa Xaa Xaa Xaa Xaa Xaa Xaa
            20                  25
```

```
<210> SEQ ID NO 4
<211> LENGTH: 29
<212> TYPE: PRT
<213> ORGANISM: Artificial sequence
<220> FEATURE:
<221> NAME/KEY: VARIANT
<222> LOCATION: (1)...(10) (20)...(29)
<223> OTHER INFORMATION: Synthesized; Xaa at poisition No. 14 is a nitrated
      tyrosine (Tyr:No2); Xaa at positions 1 to 10 and 20 to 29 denotes
      any amino acid or derivatives thereof and can be
      present or absent

<400> SEQUENCE: 4

Xaa Xaa Xaa Xaa Xaa Xaa Xaa Xaa Xaa Xaa His Arg Gly Xaa Pro Gly
1               5                   10                  15

Leu Asp Gly Xaa Xaa Xaa Xaa Xaa Xaa Xaa Xaa Xaa
            20                  25

<210> SEQ ID NO 5
<211> LENGTH: 26
<212> TYPE: PRT
<213> ORGANISM: Artificial sequence
<220> FEATURE:
<221> NAME/KEY: VARIANT
<222> LOCATION: (1)...(10) (17)...(26)
<223> OTHER INFORMATION: Synthesized; Xaa at poisition No. 13 is a nitrated
      tyrosine (Tyr:No2); Xaa at positions 1 to 10 and 17 to 26 denotes
      any amino acid or derivatives thereof and can be
      present or absent

<400> SEQUENCE: 5

Xaa Xaa Xaa Xaa Xaa Xaa Xaa Xaa Xaa Xaa Leu Gln Xaa Met Arg Ala
1               5                   10                  15

Xaa Xaa Xaa Xaa Xaa Xaa Xaa Xaa Xaa Xaa
            20                  25

<210> SEQ ID NO 6
<211> LENGTH: 9
<212> TYPE: PRT
<213> ORGANISM: Artificial sequence
<220> FEATURE:
<221> NAME/KEY: MOD_RES
<222> LOCATION: (4)
<223> OTHER INFORMATION: Synthesized; Xaa at poisition No. 4 is a nitrated
      tyrosine (Tyr:No2)

<400> SEQUENCE: 6

His Arg Gly Xaa Pro Gly Leu Asp Gly
1               5

<210> SEQ ID NO 7
<211> LENGTH: 6
<212> TYPE: PRT
<213> ORGANISM: Artificial sequence
<220> FEATURE:
<221> NAME/KEY: MOD_RES
<222> LOCATION: (3)
<223> OTHER INFORMATION: Synthesized; Xaa at poisition No. 3 is a nitrated
      tyrosine (Tyr:No2)

<400> SEQUENCE: 7

Leu Gln Xaa Met Arg Ala
1               5

<210> SEQ ID NO 8
<211> LENGTH: 9
<212> TYPE: PRT
```

```
<213> ORGANISM: Artificial sequence
<220> FEATURE:
<221> NAME/KEY: MOD_RES
<222> LOCATION: (6)
<223> OTHER INFORMATION: Synthesized; Xaa at poisition No. 6 is a nitrated
      tyrosine (Tyr:No2)

<400> SEQUENCE: 8

Gly Gly Gly Leu Gln Xaa Met Arg Ala
1               5
```